United States Patent
Cross, Jr.

(10) Patent No.: US 8,502,006 B2
(45) Date of Patent: Aug. 6, 2013

(54) DIMERIZATION PROCESS

(75) Inventor: William M. Cross, Jr., Kemah, TX (US)

(73) Assignee: Catalytic Distillation Technologies, Pasadena, TX (US)

(*) Notice: Subject to any disclaimer, the term of this patent is extended or adjusted under 35 U.S.C. 154(b) by 825 days.

(21) Appl. No.: 12/558,353

(22) Filed: Sep. 11, 2009

(65) Prior Publication Data

US 2011/0065970 A1    Mar. 17, 2011

(51) Int. Cl.
*C07C 2/16* (2006.01)

(52) U.S. Cl.
USPC ............ 585/515; 585/502; 585/520; 585/526

(58) Field of Classification Search
USPC .......................... 585/502, 510, 515, 520, 526
See application file for complete search history.

(56) References Cited

U.S. PATENT DOCUMENTS

| | | | |
|---|---|---|---|
| 2,082,006 A * | 6/1937 | Johnstone | 423/539 |
| 2,186,022 A * | 1/1940 | Holm et al. | 585/529 |
| 2,237,292 A * | 4/1941 | Deanesly | 585/515 |
| 2,670,393 A * | 2/1954 | Howerton | 585/515 |
| 4,024,203 A * | 5/1977 | Torck et al. | 585/514 |
| 4,100,220 A | 7/1978 | Bowman et al. | |
| 4,242,530 A * | 12/1980 | Smith, Jr. | 585/510 |
| 4,331,824 A | 5/1982 | Ikeda et al. | |
| 4,375,576 A | 3/1983 | Smith, Jr. | |
| 4,551,567 A | 11/1985 | Smith, Jr. | |
| 4,629,710 A | 12/1986 | Smith, Jr. | |
| 4,935,577 A * | 6/1990 | Huss et al. | 585/726 |
| 5,003,124 A | 3/1991 | Smith, Jr. et al. | |
| 5,877,372 A | 3/1999 | Evans et al. | |
| 6,335,473 B1 | 1/2002 | Bakshi et al. | |
| 6,376,731 B1 | 4/2002 | Evans et al. | |
| 6,689,927 B1 | 2/2004 | Frame et al. | |
| 6,774,275 B2 | 8/2004 | Smith, Jr. et al. | |
| 6,858,770 B2 | 2/2005 | Gelbein et al. | |
| 6,936,742 B2 | 8/2005 | Smith, Jr. | |
| 6,995,296 B2 | 2/2006 | Smith, Jr. et al. | |
| 7,145,049 B2 | 12/2006 | Loescher et al. | |
| 7,250,542 B2 | 7/2007 | Smith, Jr. et al. | |
| 7,288,693 B2 | 10/2007 | Smith, Jr. et al. | |
| 7,319,180 B2 | 1/2008 | Smith, Jr. et al. | |
| 2004/0006252 A1 | 1/2004 | Smith | |
| 2004/0210093 A1 | 10/2004 | Groten et al. | |
| 2006/0030741 A1 | 2/2006 | Smith et al. | |
| 2007/0161843 A1 | 7/2007 | Smith et al. | |
| 2007/0293711 A1 * | 12/2007 | Bakshi | 585/502 |
| 2008/0045763 A1 | 2/2008 | Cross et al. | |
| 2008/0064911 A1 | 3/2008 | Loescher et al. | |

OTHER PUBLICATIONS

Gokel, Dean's Handbook of Organic Chemistry, 2004, 2nd ed., available on-line at www.knovel.com Dec. 7, 2006.*
Woollins, "Sulfur: Inorganic Chemistry" in Encyclopedia of Inorganic Chemistry, John Wiley & Sons, available on-line Mar. 15, 2006.*
Washburn, International Critical Tables of Numerical Data, Physics, Chemistry and Technology, 1st Electronic Edition, available on-line at www.knovel.com Feb. 1, 2003.*

* cited by examiner

*Primary Examiner* — In Suk Bullock
*Assistant Examiner* — Bradley Etherton
(74) *Attorney, Agent, or Firm* — Osha Liang LLP

(57) ABSTRACT

A process for the dimerization of isoolefins is disclosed. The process may include: contacting an isoolefin with sulfurous acid in a reaction zone at conditions of temperature and pressure sufficient to dimerize at least a portion of the isoolefin.

18 Claims, 2 Drawing Sheets

DIMERIZATION PROCESS

FIELD OF THE DISCLOSURE

Embodiments disclosed herein relate generally to a process for the oligomerization of isoolefins. More specifically, embodiments disclosed herein relate to processes for the catalytic oligomerization of isoolefins, where the oligomerization is catalyzed by sulfurous acid, fed directly to the reaction zone and/or formed in situ within the reaction zone.

BACKGROUND

Isobutene is commercially significant in many applications. For example, isobutene is one of the comonomers in butyl rubber. Isobutene can also be oligomerized to produce compounds that can be used as chemical feedstock for further reacting or in gasoline blending. Diisobutene, the isobutene dimer, is of particular commercial value in several applications. For example, diisobutene can be used as an alkylation reaction feedstock or as an intermediate in the preparation of detergents. Diisobutene can also be hydrogenated to pure isooctane (2,2,4-tri-methyl pentane) that is highly preferred in gasoline blending.

Isoolefin oligomerization is a catalytic reaction that may be performed using an acid resin catalyst. For example, oligomerization of isoolefins has been disclosed in U.S. Pat. Nos. 4,242,530, 4,375,576, 5,003,124, and 7,145,049, 6,335,473, 6,774,275, 6,858,770, 6,936,742, 6,995,296, 7,250,542, 7,288,693, 7,319,180, 6,689,927, 6,376,731, 5,877,372, 4,331,824, 4,100,220 and U.S. Patent Application Publication Nos. 20080064911, 20080045763, 20070161843, 20060030741, 20040210093, and 20040006252, among others. Acid resin catalysts have also found use in various other petrochemical processes, including formation of ethers, hydration of olefins, esterifications, and expoxidations, such as described in U.S. Pat. Nos. 4,551,567 and 4,629,710.

Processes for oligomerization of olefins over such resin catalysts require periodic shutdowns of the oligomerization unit to replace and/or regenerate the catalysts. Further, such solid-catalyzed processes may require additives ("selectivators") to promote the selectivity of the catalyst to the dimer, where the additives may result in unwanted acid throw, deactivating the catalyst, and may additionally require complicated separation processes to remove the additive from the resulting product streams.

Accordingly, there exists a continuing need for improved isoolefin dimerization catalysts and processes.

SUMMARY OF THE CLAIMED EMBODIMENTS

In one aspect, embodiments disclosed herein relate to a process for the dimerization of isoolefins, the process including: contacting an isoolefin with sulfurous acid in a reaction zone at conditions of temperature and pressure sufficient to dimerize at least a portion of the isoolefin.

In another aspect, embodiments disclosed herein relate to a process for the dimerization of isoolefins, the process including: feeding a hydrocarbon mixture comprising C4 to C5 hydrocarbons including at least one of isobutene and isoamylene to a catalytic distillation reactor system having at least one reaction zone; introducing sulfurous acid to the at least one reaction zone; concurrently in the catalytic distillation reactor system: contacting the at least one of isobutene and isoamylene with the sulfurous acid in the at least one reaction zone at conditions of temperature and pressure sufficient to dimerize at least a portion of the isobutene and isoamylene to C8 to C10 hydrocarbons; separating the hydrocarbon mixture into a light hydrocarbon fraction comprising C4 to C5 hydrocarbons including any unreacted isobutene and isoamylene and a heavy fraction comprising the C8 to C10 hydrocarbons; recovering the C8 to C10 hydrocarbons from the catalytic distillation reactor systems as a bottoms fraction; and, recovering the light hydrocarbon fraction and sulfurous acid as an overheads vapor fraction.

In another aspect, embodiments disclosed herein relate to a process for the oligomerization of isoolefins, the process including: feeding a hydrocarbon mixture comprising C4 to C5 hydrocarbons including at least one of isobutene and isoamylene to a catalytic distillation reactor system having at least one reaction zone; feeding water and sulfur dioxide to the at least one reaction zone; concurrently in the catalytic distillation reactor system: contacting the water and the sulfur dioxide to form sulfurous acid; contacting the at least one of isobutene and isoamylene with the sulfurous acid in the at least one reaction zone at conditions of temperature and pressure sufficient to oligomerize at least a portion of the at least one of isobutene and isoamylene; separating the hydrocarbon mixture into a light hydrocarbon fraction comprising C4 to C5 hydrocarbons including any unreacted isobutene and isoamylene and a heavy fraction comprising the oligomers; recovering the oligomers from the catalytic distillation reactor systems as a bottoms fraction; and, recovering the light hydrocarbon fraction and sulfurous acid as an overheads vapor fraction.

Other aspects and advantages will be apparent from the following description and the appended claims.

DETAILED DESCRIPTION

Figure 1:
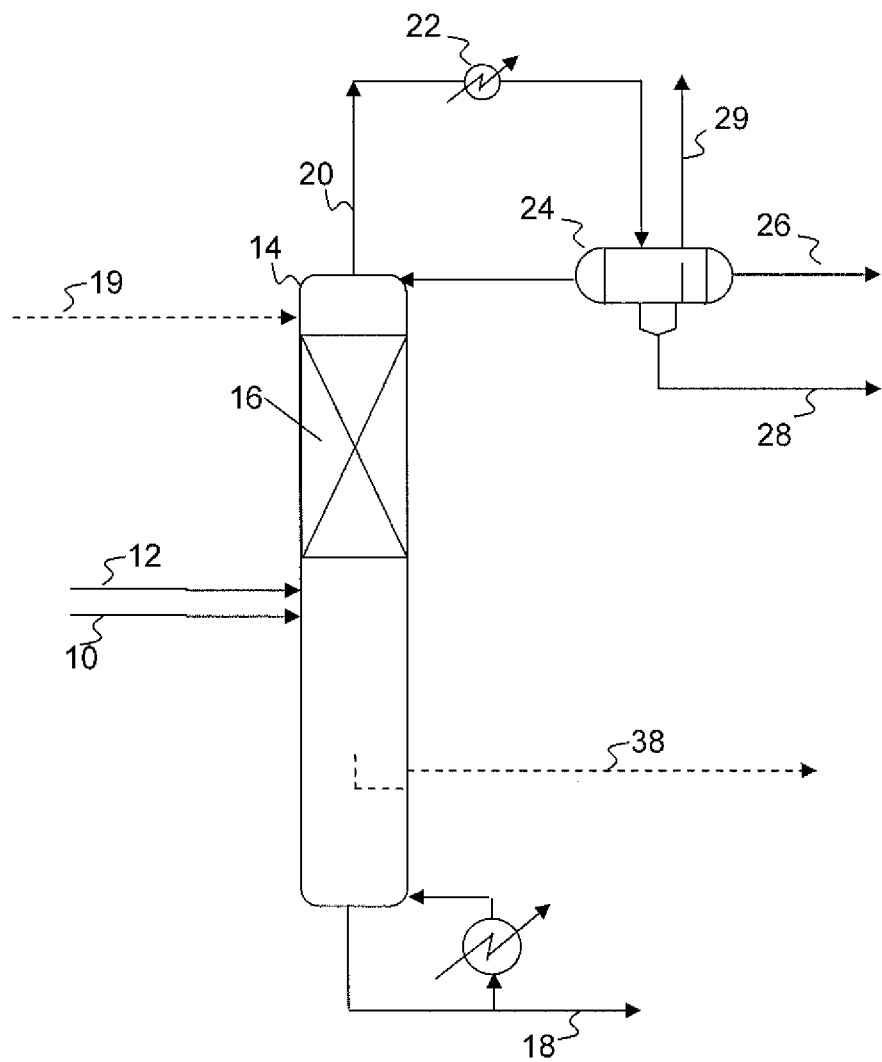
FIG. 1 is a simplified process flow diagram of a process for the production of olefin dimers according to embodiments disclosed herein.

In one aspect, embodiments herein relate to processes for the oligomerization of isoolefins. More specifically, embodiments disclosed herein relate to processes for the catalytic oligomerization of isoolefins, where the oligomerization is catalyzed by sulfurous acid, fed directly to the reaction zone and/or formed in situ within the reaction zone.

In some embodiments, the oligomerization process may include contacting an isoolefin with sulfurous acid in a reaction zone at conditions of temperature and pressure sufficient to oligomerize at least a portion of the isoolefin, where the oligomers are preferably dimers and trimers, and in some embodiments the oligomerization is selective to form the dimer. "Dimers," "trimers," and "oligomers" as used herein may include reaction products of an isoolefin with itself, such as isobutene dimers (a C8 hydrocarbon) or isoamylene dimers (a C10 hydrocarbon), as well as co-dimers, co-trimers, and co-oligomers, such as resulting from the reaction of isobutene with isoamylene. The oligomerization processes disclosed herein may be conducted in any type of oligomerization reactor, and in various embodiments the oligomerization may be conducted in a catalytic distillation reactor system.

The hydrocarbon feed to the oligomerization reactor(s) may include purified isoolefin streams, such as a feed stream containing, isobutene, isoamylenes, or mixtures thereof. In other embodiments, oligomerization feeds may include a $C_4$-$C_5$, a $C_4$ or a $C_5$ light naphtha cut. When present in mixtures, the tertiary olefins, such as isobutene and isoamylenes, are more reactive than the normal olefin isomers and are preferentially dimerized or oligomerized. The primary oligomerization products are dimers and trimers of the $C_4$ to $C_5$ olefins. The isoalkanes in the $C_4$ to $C_5$ light naphtha cuts may include isobutane, isopentane or mixtures thereof, which may act as a diluent in the oligomerization reactor.

The primary oligomer products may include dimers and trimers of isoolefins. For example, isobutene may be oligomerized to form a $C_8$ or $C_{12}$ tertiary olefin, isopentene may be oligomerized to form a $C_{10}$ or $C_{15}$ tertiary olefin, and mixtures of isobutene and isopentene may be reacted to form $C_8$ to $C_{15}$ tertiary olefins, among other products. $C_6$ to $C_{16}$ olefin oligomers may also be prepared from $C_3$ to $C_5$ olefins. In some embodiments, the oligomers have 8 to 16 carbon atoms and correspond to oligomers which are prepared from $C_4$ to $C_5$ olefins. The oligomerization of the tertiary olefin may also be performed when carried out on a light naphtha stream with the separation of normal olefins being easily achieved by fractionation from the heavier (higher boiling) oligomers (mainly dimers and trimers).

Within the scope of this application, the expression "catalytic distillation reactor system" denotes an apparatus in which the catalytic reaction and the separation of the products take place at least partially simultaneously. The apparatus may comprise a conventional catalytic distillation column reactor, where the reaction and distillation are concurrently taking place at boiling point conditions, or a distillation column operatively connected with at least one side reactor to which a sidedraw from the distillation column is introduced as a feed and from which a reactor effluent is withdrawn and returned to the distillation column, where the side reactor may be operated as a liquid phase reactor, a vapor phase reactor, or a boiling point reactor. While both catalytic distillation reactor systems described may be preferred over conventional liquid phase reaction followed by separations, a catalytic distillation column reactor may have the advantages of decreased piece count, reduced capital cost, increased catalyst productivity per pound of catalyst, efficient heat removal (heat of reaction may be absorbed into the heat of vaporization of the mixture), and a potential for shifting equilibrium. Divided wall distillation columns, where at least one section of the divided wall column contains a catalytic distillation structure, may also be used, and are considered "catalytic distillation reactor systems" herein.

Processes disclosed herein may include any number of reactors, including catalytic distillation reactor systems, both up-flow and down-flow. Use of catalytic distillation reactor systems may prevent foulants and heavy catalyst poisons in the feed from building up within the reaction zone(s). In addition, clean reflux may continuously wash the catalytic distillation structure in the reaction zone. These factors combine to provide a long catalyst life. The heat of reaction evaporates liquid and the resulting vapor is condensed in the overhead condenser to provide additional reflux. The resulting temperature profile in the reaction zone in the catalytic distillation reaction system is much closer to an isothermal catalyst bed rather than the adiabatic temperature increase typical of conventional fixed bed reactors.

Other reactors useful in embodiments disclosed herein may include traditional fixed bed reactors, boiling point reactors, and pulsed flow reactors, where the reactant flow and product flow may be co-current or counter-current. Boiling point and pulsed flow reactors may also provide for a continuous washing of the catalyst in addition to capturing at least a portion of the heat of reaction through evaporation, allowing for an improved reactor temperature profile as compared to conventional fixed bed reactors. Reactors useful in embodiments disclosed herein may be used as a stand-alone reactor or may be used in combination with one or more reactors of the same or different type.

Any type of reactor may be used to carry out the reactions described herein. The examples of reactors suitable for carrying out the reactions involving isoolefin dimerization or oligomerization reactions may include distillation column reactors, divided wall distillation column reactors, traditional tubular fixed bed reactors, bubble column reactors, slurry reactors equipped with or without a distillation column, pulsed flow reactors, catalytic distillation columns wherein slurry solid catalysts flow down the column, or any combination of these reactors. Multiple reactor systems useful in embodiments disclosed herein may include a series of multiple reactors or multiple reactors in parallel for the first reaction zone. A person of ordinary skill in the art would recognize that other types of reactors may also be used.

The oligomerization reactors useful in embodiments disclosed herein may include any physical devices or a combination of two or more devices, including reactors and reactor systems as described above. The reactor(s) may have various internal devices for vapor-liquid separation and vapor/liquid traffic. Reaction zones within the reactor(s) may include structure and/or packing "wettable" by water and sulfurous acid, thereby retaining or holding up at least a portion of the sulfurous acid on the surface of the structure or packing, providing for the contact of the isoolefin with the catalyst (sulfurous acid) to promote the desired dimerization reaction. The wettable structure should suitably have sufficient resistance to attack by sulfurous acid and other compounds in the reactor feeds and products.

Wettable structure and packing useful in embodiments disclosed herein may include various distillation structures and packing materials, which may be catalytic or non-catalytic. A significant amount of sulfurous acid is held up on the wettable packing. Reaction is believed to take place between the hydrocarbon phase and the aqueous sulfurous acid phase dispersed on the wettable packing. Olefin continuously dissolves into the acid phase and dimer/oligomer product is continuously extracted into the hydrocarbon phase.

Suitable wettable structure and packing may include, for example, random or dumped distillation packings which are: catalytically inert dumped packings that contain higher void fraction and maintain a relatively large surface area, such as, Berl Saddles (Ceramic), Raschig Rings (Ceramic), Raschig Rings (Steel), Pall rings (Metal), Pall rings (Plastic, e.g. polypropylene) and the like. Monoliths, which are structures containing multiple, independent, vertical channels and may be constructed of various materials such as plastic, ceramic, or metals, in which the channels are typically square, are also suitable wettable structures. Other geometries could also be used.

Other materials that promote the distribution of liquid and vapors may also be used, including mist eliminators, demisters, or other wire or multi-filament type structure. Such multi-filament structures may include one or more of fiberglass, steel, Teflon, polypropylene, polyethylene, polyvinylidenedifluroride (PVDF), polyester, or other various materials, which may be knitted (or co-knit, where more than one type of filament or wire structure is used), woven, non-woven, or any other type of multi-filament structure. Structures including multifilament wires as typically used in demister services, structures including an element of woven fiberglass cloth, and high surface area stainless steel structured packings are preferred.

Reactors according to embodiments disclosed herein may include one or multiple dimerization reaction zones, where each may provide structure for the contact of the isoolefin with the sulfurous acid. Sulfurous acid may be introduced to the reaction zone by feeding sulfurous acid to the reaction zone or by forming sulfurous acid in situ within the reaction zone by contacting water with sulfur dioxide. The contact structures used may thus be "wettable" by water, the aqueous holdup on the contact structure admixing with sulfur dioxide and forming the sulfurous acid in situ within the reaction zone.

When introduced to a catalytic distillation reactor system, the sulfurous acid and/or sulfur dioxide is preferably introduced to the column at a feed point within or below the lowermost reaction zone or within or below each respective reaction zone, the sulfurous acid and/or sulfur dioxide distilling upward within the column and dispersing into the reaction zone, wetting the contact structure and providing for the desired catalytic activity within the reaction zone.

When forming sulfurous acid in situ, water may be introduced to the reaction zone as an independent feed, or may be admixed with the isoolefin feed prior to introduction to the reactor. In some embodiments, water may be present in the isoolefin-containing hydrocarbon feed below or at saturation levels. In other embodiments, water may be admixed with the hydrocarbon feed to above saturation levels (free water present as a separate phase). In other embodiments, the hydrocarbon feed to the column may be split, where only a portion of the hydrocarbon feed is admixed with water prior to feeding of the mixed stream to the reactor.

In some embodiments, the isoolefin-containing hydrocarbon feed may contain various water-soluble impurities, such as nitrites. In such instances, the hydrocarbon feed may be water-washed to remove the nitrites and other water-soluble impurities, where the resulting hydrocarbon raffinate may contain sufficient water for forming sulfurous acid in situ within the reaction zone.

If necessary or desired, the saturation level of the hydrocarbon feed may be adjusted prior to admixture or contact with water. For example, water solubility increases with increasing temperature, and thus heating of the hydrocarbon feed prior to admixture with water may provide for a higher concentration of water to be dissolved within the hydrocarbon phase and transported to the reactor.

The resulting dimers may be used, for example, as a raw material for the production of various chemicals, such as herbicides and pesticides. In other embodiments, the dimer may be fed to an alkylation system, where the dimer may dissociate into constituent olefins and react with an alkane to produce an alkylate in the gasoline-boiling range. The dimer may also be hydrogenated to form gasoline-range hydrocarbons, such as iso-octane, iso-nonane, and other hydrocarbons. In yet other embodiments, the dimer containing stream may be used as a gasoline-range hydrocarbon blendstock without hydrogenation or alkylation.

Referring now to FIG. 1, a process for the oligomerization (dimerization) of isoolefins according to embodiments disclosed herein is illustrated. Sulfurous acid (or sulfurous acid constituents, such as sulfur dioxide and/or water) and a wet or dry hydrocarbon feedstock, such as a mixed C4 or C4/C5 hydrocarbon stream containing isoolefins, may be fed via flow lines 10 and 12, respectively, to catalytic distillation reactor system 14. Catalytic distillation reactor system 14 may include one or more reaction zones 16 containing wettable contact structures to provide the necessary sulfurous acid holdup and the desired reactivity to convert at least a portion of the isoolefins to dimer or oligomer products. Other portions of catalytic distillation reactor system 14 may include trays or packing (not illustrated) to perform the separation of the feed components and reaction products.

Various options exist for the locating the sulfurous acid feed point or the sulfurous acid constituent feed(s) to catalytic distillation reactor system 14. The location of the feed points may depends on numerous factors, including the feed composition, feed rate, level of feed contaminants, and temperature and pressure operating conditions, among others.

As illustrated in FIG. 1, the hydrocarbon and sulfurous acid are fed below the reaction zone 16. The compounds distill upward within column 14, contacting within reaction zone 16 to produce the desired dimer or oligomer products, which distill downward within the column 14 and is recovered as bottoms product stream 18. Water and/or sulfurous acid injection can optionally or additionally be provided via feed line 19.

The inert C4 and/or C5 components, such as n-butane, n-pentanes, isobutane, and isopentanes, among others, as well as unreacted C4 and C5 isoolefins, water, and sulfurous acid distill upward within column 14 and are recovered as an overhead vapor fraction via flow line 20. The sulfurous acid and/or the water may form various azeotropes with the hydrocarbons within column 14 and the overhead system. The hydrocarbons, water, and sulfurous acid may then be cooled and condensed via heat exchanger 22 and collected in overhead drum 24, which may provide for the separation of the condensate into organic and aqueous fractions, which may be recovered via flow lines 26 and 28, respectively. Light ends, including excess $SO_2$ feed, may be vented via flow line 29.

When the feed(s) to catalytic distillation reactor system 14 include certain contaminants, such as amines, salts may be formed as reaction byproducts. For instance, in the case of nitrites in the feed, nitrites will react with the sulfurous acid to produce ammonium bisulfite and a carboxylic acid. ($CH_3CN+H_2SO_3+2H_2O \rightarrow CH_3COOH+(NH_4)HSO_3$).

Flushing of these salts and reaction byproducts may be required to keep these materials from being caught in the column and to maintain sufficient sulfurous acid strength for reaction within the packed section. To flush salts from the system, at least one aqueous draw 38 may be provided below packed reaction zone 16. Additionally, to make up strength and/or water to the system (as water is being removed via the salt formation), a water addition and/or a sulfurous acid feed 19 may be provided above reaction zone 16 with sulfur dioxide or sulfurous acid added via flow line 10 below reaction zone 16.

When the feed is essentially clean of salt precursors and the sulfurous acid (in equilibrium with $SO_2$ and water at the given pressure and temperature on each tray) is held in the packed section, water and sulfurous acid form an azeotrope, are condensed and collected as an overhead product in the overhead accumulator 24, and drained as an aqueous phase from the system via flow line 28.

Regardless of the feed contaminant levels, $SO_2$ and water feeds are adjusted to maintain a concentration of sulfurous acid within the packed section sufficient to catalyze the desired oligomerization reaction.

Figure 2:
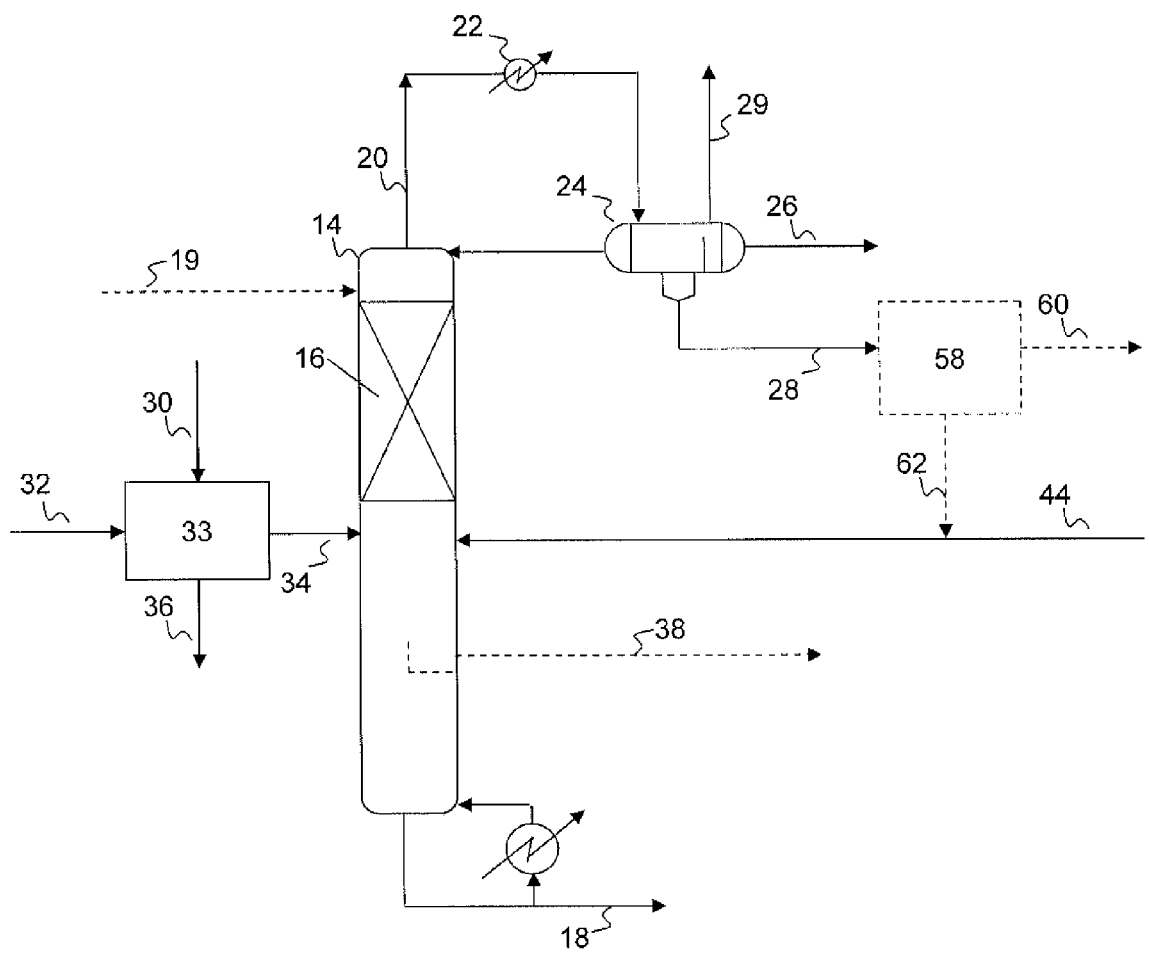
FIG. 2 is a simplified process flow diagram of a process for the production of olefin dimers according to embodiments disclosed herein.

Referring now to FIG. 2, a process for the oligomerization (dimerization) of isoolefins according to embodiments disclosed herein is illustrated, where like numerals represent like parts. In this embodiment, the sulfurous acid is formed in situ within the catalytic distillation reactor system. Water and a hydrocarbon feedstock, such as a mixed C4 or C4/C5 hydrocarbon stream containing isoolefins, may be fed via flow lines 30 and 32, respectively, to a vessel or system, such as a water wash system, for contacting of the water and the hydrocarbons to produce a wet hydrocarbon stream 34 and aqueous stream 36. Wet hydrocarbon stream 34 may contain water up to, equal to, or greater than saturation levels. If necessary or desired, hydrocarbon stream may be heated, such as by indirect heat exchange (not shown), prior to contact with water in system 33, thereby adjusting the solubility of water in the hydrocarbons, or the solubility of various feed impurities, such as nitrogen-containing compounds, in the water/aqueous phase, to a desired level.

The wet hydrocarbon feedstock may then be fed to catalytic distillation reactor system 14 having one or more reaction zones 16 containing wettable contact structures. Other portions of catalytic distillation reactor system 14 may include trays or packing (not illustrated) to perform the separation of the feed components and reaction products. Sulfur dioxide is also fed to catalytic distillation reactor system 14 via flow line 44.

The sulfur dioxide, water, and hydrocarbons distill upward within the column, the water wetting the contact structures within reaction zone 16. Sulfur dioxide may then react with the water to form sulfurous acid in situ within reaction zone 16 and catalyzing the reaction to convert at least a portion of the isoolefins to desired dimer or oligomer products, which distill downward within the column 14 and are recovered as bottoms product stream 18.

The inert C4 and/or C5 components, such as n-butane, n-pentanes, isobutane, and isopentanes, among others, as well as unreacted C4 and C5 isoolefins, water, and sulfurous acid distill upward within column 14 and are recovered as an overhead vapor fraction via flow line 20. The hydrocarbons, water, and sulfurous acid may then be cooled and condensed via heat exchanger 22 and collected and separated in overhead drum 24, the condensate organic and aqueous fractions, including sulfurous acid, being recovered via flow lines 26 and 28, respectively.

Optionally, the aqueous fraction recovered via flow line 28 may be fed to system 58 to dissociate sulfurous acid into water and sulfur dioxide. The dissociate product may then be separated to recover a water fraction via flow line 60 and a sulfur dioxide fraction via flow line 62. The sulfur dioxide in flow line 62, or a portion thereof, may then be recycled to catalytic distillation reactor system 14, such as by combination with sulfur dioxide feed 44.

As noted above, the resulting dimers and oligomers may be used in various downstream processes. Likewise, the raffinate hydrocarbon streams recovered (flow line 26, for example) may also be used directly or indirectly in various downstream processes. Further, water stream 60, or a portion thereof, may be recycled to water contact system 33 to decrease or minimize the amount of fresh water added to the system and the amount of waste water to be processed by the production facility.

Operating conditions within catalytic distillation reactor systems for dimerizing isoolefins as described above may include temperatures and pressures sufficient for a) recovery of the unreacted C4 and/or C5 hydrocarbons, water, and sulfurous acid as an overhead vapor fraction, b) the desired reactivity of the isoolefins over the sulfurous acid, and c) recovery of the dimer as a bottoms liquid fraction. The temperature within the reaction zone may thus be intimately linked to the pressure, the combination of which provides for boiling of the isoolefin and water within the reaction zone(s). Higher temperatures may be required in portions of the column below the reaction zone, thus providing for the separation of the dimer from the unreacted feed compounds. In some embodiments, the temperature in the reaction zone(s) may be in a range from about 10° C. to about 121 (about 50° F. to about 250° F.); from about 37° C. to about 94° C. (about 100° F. to about 200° F.) in other embodiments; and from about 51° C. to about 80° C. (about 125° F. to about 175° F.) in yet other embodiments, such as from about 57° C. to about 63° C. (about 135° F. to about 145° F.). Pressures within the column may range from subatmospheric (about 0.5 bar (7 psia), for example) to about 14 bar (200 psia) in some embodiments; from about 3.4 bar to about 10.3 bar (about 50 to about 150 psia) in other embodiments; and from about 5.1 bar to about 8.6 bar (about 75 to about 125 psia) in yet other embodiments.

EXAMPLES

To the author's surprise, isobutylene dimers were produced during a distillation pilot test. The distillation column was set up to fractionate C4 material from C5+ material. The distillation column contained two feed streams. The first feed was a mixed paraffinic hydrocarbon stream containing approximately 75 wt % C4 paraffins, some trace $SO_2$ (approximately 10-20 ppm Sulfur), and the remainder C5+ material. The second feed stream contained approximately 40 wt % isobutylene with the remainder isobutane, and water of saturation. (approximately 300 ppm $H_2O$). Both feeds were introduced below a packed section of ⅝" stainless steel pall rings. Operating conditions for the test are provided in Table 1.

TABLE 1

| Operating Conditions | | |
| --- | --- | --- |
| Condition | Value | Value |
| Overhead Temperature | 51.1° C. | 124° F. |
| Bottoms Temperature | 165.5° C. | 330° F. |
| Paraffin Feed (containing C4 & C5+) | 29.5 kg/h | 65 lb/hr |
| Olefin Feed (iC4 & iC4=) | 10.4 kg/h | 23 lb/hr |
| Bottoms Flow | 8.2 kg/h | 18 lb/hr |
| Overhead Pressure | 6.2 bar | 85 psig |

Under the conditions in Table 1, a portion of the isobutylene was converted to dimers of isobutylene, namely 2,4,4 trimethyl-1-pentene & 2,4,4 trimethyl-2-pentene. These dimers were produced within the distillation column and taken out as column bottoms along with the C5+ paraffin fractions which came in with the feed. Table 2 provides the relative quantity of dimer produced in the bottoms stream.

TABLE 2

| Bottoms Fraction analysis (average from run hours 640 to 700) | | | |
| --- | --- | --- | --- |
| Component | Weight percent | Component | Weight percent |
| n-butane | 1.584 | 2,3,3-trimethyl pentane | 8.142 |
| Trans-2-butene | 0.609 | 2,3-dimethyl hexane | 0.904 |
| Cis-2-butene | 0.551 | 2,2,5-trimethyl hexane | 3.655 |
| 3-methyl-1-butene | 0.006 | 2,3,4-trimethyl hexane | 0.555 |
| iso-pentane | 6.595 | 2,4-dimethyl heptane | 0.050 |
| n-pentane | 0.020 | 2,6-dimethyl heptane | 0.131 |
| 2-methyle-2-butene | 0.038 | 2,5-dimethyl heptane | 0.018 |
| 2,3-dimethyl butane | 5.048 | 2,2,4-trimethyl heptane | 0.585 |
| 2-methyl pentane | 0.733 | 3,3,5-trimethyl heptane | 0.222 |
| 3-methyl pentane | 0.436 | 2,3,6-trimethyl heptane | 0.179 |
| 2,4-dimethyl pentenee | 3.165 | 2,3,5-trimethyl heptane | 0.127 |
| 2,2,3-trimethyl butane | 0.250 | trimethyl heptane | 0.797 |
| 2-methyl hexane | 0.065 | 2,2,6-trimethyloctane | 1.563 |
| 2,3-dimethyl pentane | 1.689 | C8's | 0.499 |
| 3-methyl hexane | 0.049 | C9's | 1.160 |
| 2,2,4-trimethyl pentane | 22.014 | C10's | 0.192 |

TABLE 2-continued

Bottoms Fraction analysis (average from run hours 640 to 700)

| Component | Weight percent | Component | Weight percent |
|---|---|---|---|
| 2,4,4-trimethyl-1-pentene | 5.250 | C11's | 0.059 |
| 2,4,4-trimethyl-2-pentene | 1.273 | C12's | 2.598 |
| 2,5-dimethyl hexane | 3.780 | C14's | 6.229 |
| 2,4-dimethyl hexane | 2.762 | C15's | 4.197 |
| 2,3,4-trimethyl pentane | 7.635 | Heavies | 4.591 |

To determine the means by which the dimers were being produced, water was removed from the isobutylene/isobutane feed stream using a mole sieve dryer. $SO_2$ continued to be introduced via the paraffin stream, and the bottoms product was monitored over time. Table 3. provides the data on the bottoms dimer quantity over sample periods after removal of the water. Once water was removed from the system, dimer production stopped, as shown by Table 3.

As described above, embodiments disclosed herein provide for the oligomerization of isoolefins using sulfurous acid. Advantageously, embodiments disclosed herein react isoolefins to form dimers in a catalytic distillation reactor system, where the concurrent reaction and separation provide for the efficient formation and removal of dimers from the reaction zone, thereby limiting the extent of reaction and the formation of undesirable higher oligomers and polymers.

The use of an aqueous acid phase to catalyze the oligomerization reaction may also provide for long term reactor stability, avoiding fouling and other problems commonly associated with use of solid or heterogeneous catalysts. Catalyst regeneration cycles and periodic catalyst replacement can also be negated with use of sulfurous acid, thereby improving process operating costs substantially, although metallurgy (affecting capital costs) may need to be adjusted to account for the presence of sulfurous acid.

The selectivity and operability of embodiments disclosed herein may additionally relax the need for oligomerization reaction modifiers and the associated separation equipment commonly used for oligomerization reaction systems. For example, alcohols and tertiary ethers, such as tertiary butyl alcohol (TBA) and methyl tertiary butyl ether (MTBE), are commonly used to promote selectivity of a heterogeneous oligomerization catalyst to the dimer. Embodiments disclosed herein may require no reaction modifiers while providing a high selectivity toward the dimer and/or trimer, thus negating the capital and operating costs commonly associated with these reaction modifiers. The associated capital and operating cost savings may more than offset the increased costs due to metallurgical requirements.

TABLE 3

Bottoms fraction analysis over time after water removal.

| | Run Hours | | |
|---|---|---|---|
| Component | 700 | 712 | 724 |
| n-butane | 2.245 | 0.603 | 1.560 |
| Trans-2-butene | 0.903 | 0.112 | 0.017 |
| Cis-2-butene | 0.755 | 0.097 | 0.008 |
| 3-methyl-1-butene | 0.010 | 0.000 | 0.000 |
| iso-pentane | 6.762 | 5.914 | 7.271 |
| n-pentane | 0.021 | 0.013 | 0.017 |
| 2-methyle-2-butene | 0.037 | 0.000 | 0.000 |
| 2,3-dimethyl butane | 4.958 | 5.054 | 5.636 |
| 2-methyl pentane | 0.772 | 0.774 | 0.823 |
| 3-methyl pentane | 0.502 | 0.488 | 0.514 |
| 2,4-dimethyl pentenee | 3.512 | 3.586 | 3.737 |
| 2,2,3-trimethyl butane | 0.211 | 0.234 | 0.256 |
| 2-methyl hexane | 0.058 | 0.070 | 0.072 |
| 2,3-dimethyl pentane | 2.073 | 2.106 | 2.183 |
| 3-methyl hexane | 0.045 | 0.054 | 0.055 |
| 2,2,4-trimethyl pentane | 21.204 | 21.505 | 21.948 |
| 2,4,4-trimethyl-1-pentene | 4.685 | 1.335 | 0.000 |
| 2,4,4-trimethyl-2-pentene | 1.068 | 0.309 | 0.000 |
| 2,5-dimethyl hexane | 4.508 | 4.529 | 4.630 |
| 2,4-dimethyl hexane | 3.027 | 3.088 | 3.067 |
| 2,3,4-trimethyl pentane | 8.067 | 8.242 | 8.195 |
| 2,3,3-trimethyl pentane | 8.232 | 8.669 | 8.590 |
| 2,3-dimethyl hexane | 0.988 | 1.008 | 0.980 |
| 2,2,5-trimethyl hexane | 2.515 | 3.318 | 3.580 |
| 2,3,4-trimethyl hexane | 0.423 | 0.541 | 0.576 |
| 2,4-dimethyl heptane | 0.031 | 0.043 | 0.044 |
| 2,6-dimethyl heptane | 0.080 | 0.108 | 0.130 |
| 2,5-dimethyl heptane | 0.000 | 0.000 | 0.019 |
| 2,2,4-trimethyl heptane | 0.562 | 0.724 | 0.781 |
| 3,3,5-trimethyl heptane | 0.162 | 0.216 | 0.223 |
| 2,3,6-trimethyl heptane | 0.150 | 0.192 | 0.202 |
| 2,3,5-trimethyl heptane | 0.118 | 0.141 | 0.145 |
| trimethyl heptane | 0.566 | 0.717 | 0.779 |
| 2,2,6-trimethyloctane | 1.573 | 1.983 | 2.046 |
| C8's | 0.430 | 0.421 | 0.395 |
| C9's | 0.715 | 1.280 | 1.351 |
| C10's | 0.332 | 0.000 | 0.000 |
| C11's | 0.034 | 0.043 | 0.071 |
| C12's | 2.741 | 2.142 | 1.676 |
| C14's | 7.335 | 7.740 | 7.705 |
| C15's | 3.449 | 6.236 | 6.236 |
| Heavies | 4.138 | 6.368 | 4.481 |

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed:

1. A process for the dimerization of isoolefins, the process comprising:
    feeding a hydrocarbon mixture comprising C4 to C5 hydrocarbons including at least one of isobutene and isoamylene to a catalytic distillation reactor system having at least one reaction zone;
    introducing sulfurous acid to the at least one reaction zone;
    concurrently in the catalytic distillation reactor system:
        contacting the at least one of isobutene and isoamylene with the sulfurous acid in the at least one reaction zone at conditions of temperature and pressure sufficient to dimerize at least a portion of the isobutene and isoamylene to C8 to C10 hydrocarbons;
        separating the hydrocarbon mixture into a light hydrocarbon fraction comprising C4 to C5 hydrocarbons including any unreacted isobutene and isoamylene and a heavy fraction comprising the C8 to C10 hydrocarbons;
    recovering the C8 to C10 hydrocarbons from the catalytic distillation reactor systems as a bottoms fraction;
    recovering the light hydrocarbon fraction and sulfurous acid as an overheads vapor fraction.

2. The process of claim 1, wherein the introducing sulfurous acid comprises feeding sulfurous acid to the catalytic distillation reactor system to a feed location within or below the at least one reaction zone.

3. The process of claim 1, wherein the introducing sulfurous acid comprises forming the sulfurous acid in situ in the at least reaction zone by contacting water with sulfur dioxide.

4. The process of claim 3, further comprising feeding sulfur dioxide to the catalytic distillation reactor system.

5. The process of claim 3, further comprising at least one of:
feeding water to the catalytic distillation reactor system; and
admixing water and the hydrocarbon mixture prior to the feeding of the hydrocarbon mixture to the catalytic distillation reactor system.

6. The process of claim 5, wherein the admixing comprises water washing the hydrocarbon mixture.

7. The process of claim 1, further comprising condensing and separating the overheads vapor fraction to recover an aqueous fraction comprising at least one of water and sulfurous acid and an organic fraction comprising the light hydrocarbon fraction.

8. The process of claim 7, further comprising recycling at least a portion of the aqueous fraction to the catalytic distillation reactor system below the at least one reaction zone.

9. The process of claim 7, further comprising feeding at least a portion of the organic fraction to the catalytic distillation reactor system as a reflux.

10. The process of claim 7, further comprising:
dissociating the sulfurous acid in the aqueous fraction to form water and sulfur dioxide; and
recycling at least a portion of the sulfur dioxide from the dissociating to the catalytic distillation reactor system.

11. The process of claim 1, further comprising at least one of:
using the C8 to C10 hydrocarbons as a gasoline blend component;
alkylating the C8 to C10 hydrocarbons to form gasoline boiling range hydrocarbons;
hydrogenating the C8 to C10 hydrocarbons.

12. A process for the oligomerization of isoolefins, the process comprising:
feeding a hydrocarbon mixture comprising C4 to C5 hydrocarbons including at least one of isobutene and isoamylene to a catalytic distillation reactor system having at least one reaction zone;
feeding water and sulfur dioxide to the at least one reaction zone;
concurrently in the catalytic distillation reactor system:
contacting the water and the sulfur dioxide to form sulfurous acid;
contacting the at least one of isobutene and isoamylene with the sulfurous acid in the at least one reaction zone at conditions of temperature and pressure sufficient to oligomerize at least a portion of the at least one of isobutene and isoamylene;
separating the hydrocarbon mixture into a light hydrocarbon fraction comprising C4 to C5 hydrocarbons including any unreacted isobutene and isoamylene and a heavy fraction comprising the oligomers;
recovering the oligomers from the catalytic distillation reactor systems as a bottoms fraction;
recovering the light hydrocarbon fraction and sulfurous acid as an overheads vapor fraction.

13. The process of claim 12, further comprising admixing water and the hydrocarbon mixture prior to the feeding of the hydrocarbon mixture to the catalytic distillation reactor system.

14. The process of claim 13, wherein the admixing comprises water washing the hydrocarbon mixture.

15. The process of claim 12, further comprising condensing and separating the overheads vapor fraction to recover an aqueous fraction comprising at least one of water and sulfurous acid and an organic fraction comprising the light hydrocarbon fraction.

16. The process of claim 15, further comprising recycling at least a portion of the aqueous fraction to the catalytic distillation reactor system below the at least one reaction zone.

17. The process of claim 15, further comprising feeding at least a portion of the organic fraction to the catalytic distillation reactor system as a reflux.

18. The process of claim 15, further comprising:
dissociating the sulfurous acid in the aqueous fraction to form water and sulfur dioxide; and
recycling at least a portion of the sulfur dioxide from the dissociating to the catalytic distillation reactor system.

* * * * *